US00PP27301P3

(12) United States Plant Patent
Ranney

(10) Patent No.: US PP27,301 P3
(45) Date of Patent: Oct. 25, 2016

(54) ***LIGUSTRUM* PLANT NAMED 'NCLX1'**

(50) Latin Name: *Ligustrum*
Varietal Denomination: NCLX1

(71) Applicant: North Carolina State University, Raleigh, NC (US)

(72) Inventor: Thomas G. Ranney, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 173 days.

(21) Appl. No.: 14/121,065

(22) Filed: Jul. 25, 2014

(65) Prior Publication Data

US 2016/0029531 P1 Jan. 28, 2016

(51) Int. Cl.
*A01H 5/00* (2006.01)

(52) U.S. Cl.
USPC ..... Plt./226

(58) Field of Classification Search
USPC ..... Plt./226
See application file for complete search history.

(56) References Cited

PUBLICATIONS

Flowering Shrubs, Spring Meadow Nursery, Inc. Starter Plants Catalog and Shrub Reference 2013-2014; Aug. 25, 2013, pp. 61 (Golden Ticket).

*Primary Examiner* — Keith Robinson
(74) *Attorney, Agent, or Firm* — Myers Bigel & Sibley, P.A.

(57) ABSTRACT

'NCLX1' is a new cultivar of privet with bright, yellow-colored foliage, compact form with dense branching habit, fragrant white flowers from late-May to June, and low-fertility with limited fruit set.

3 Drawing Sheets

Latin name of the genus and species: The Latin name of the novel plant variety disclosed herein is *Ligustrum*. 'NCLX1' is a complex interspecific hybrid, *Ligustrum [Ligustrum×vicaryi (ovalifolium×vulgare)]* by *Ligustrum tschonoskii.*

Variety denomination: The inventive variety of *Ligustrum* disclosed herein has been given the varietal denomination 'NCLX1'.

BACKGROUND OF THE INVENTION

The present invention comprises a new and distinct variety of *Ligustrum*, hereinafter referred to by the cultivar name 'NCLX1'. This new privet was developed through a breeding program at North Carolina State University, Mills River, N.C. 'NCLX1' was selected from a population of seedlings generated by hybridizing *Ligustrum×vicaryi* (unpatented) with *Ligustrum tschonoskii* 'Little Thomas' (unpatented). The first asexual propagation of 'NCLX1' was carried out in July 2010 by rooting stem cuttings at the North Carolina State University, Mountain Horticultural Crops Research Station, Mills River, N.C. and 'NCLX1' has been asexually reproduced repeatedly by vegetative cuttings over a 3-year period. 'NCLX1' roots readily from softwood cuttings treated with a basal dip of 2,500-5,000 ppm indole butyric acid (potassium salt) in water. It takes about 4 to 6 weeks for stem cuttings to initiate roots and a well-rooted plant can be produce within 12 to 14 weeks. 'NCLX1' has been found to retain its distinctive characteristics through successive asexual propagations.

SUMMARY OF THE INVENTION

The following are the most outstanding and distinguishing characteristics of this new cultivar when grown under standard horticultural practices at North Carolina State University, Mountain Horticultural Crops Research Station, Mills River, N.C.

1. Bright, yellow-colored foliage.
2. Compact form with dense branching habit.
3. Fragrant white flowers from late-May to June.
4. Low-fertility with limited fruit set.

BRIEF DESCRIPTION OF THE DRAWINGS

This new privet is illustrated by the accompanying photographs which show the plant's form, foliage and inflorescences. The colors shown are as true as can be reasonably obtained by conventional photographic procedures. Colors in the photographs may differ slightly from the color values cited in the detailed botanical description, which accurately describe the colors of the new privet.

DETAILED BOTANICAL DESCRIPTION

Figure 1:
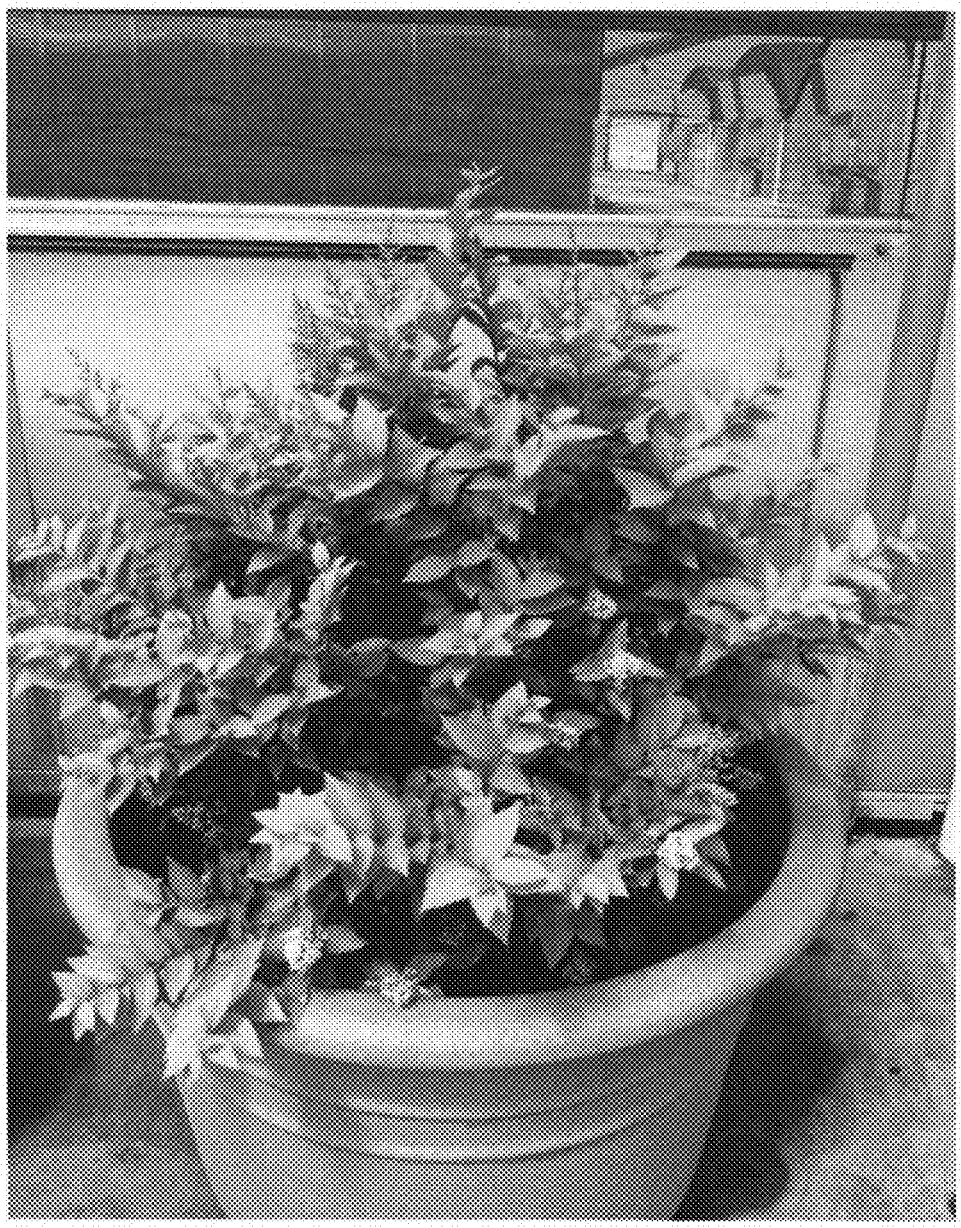
FIG. 1 shows the overall compact habit of a container-grown plant of 'NCLX1' that is two years old.
Figure 2:
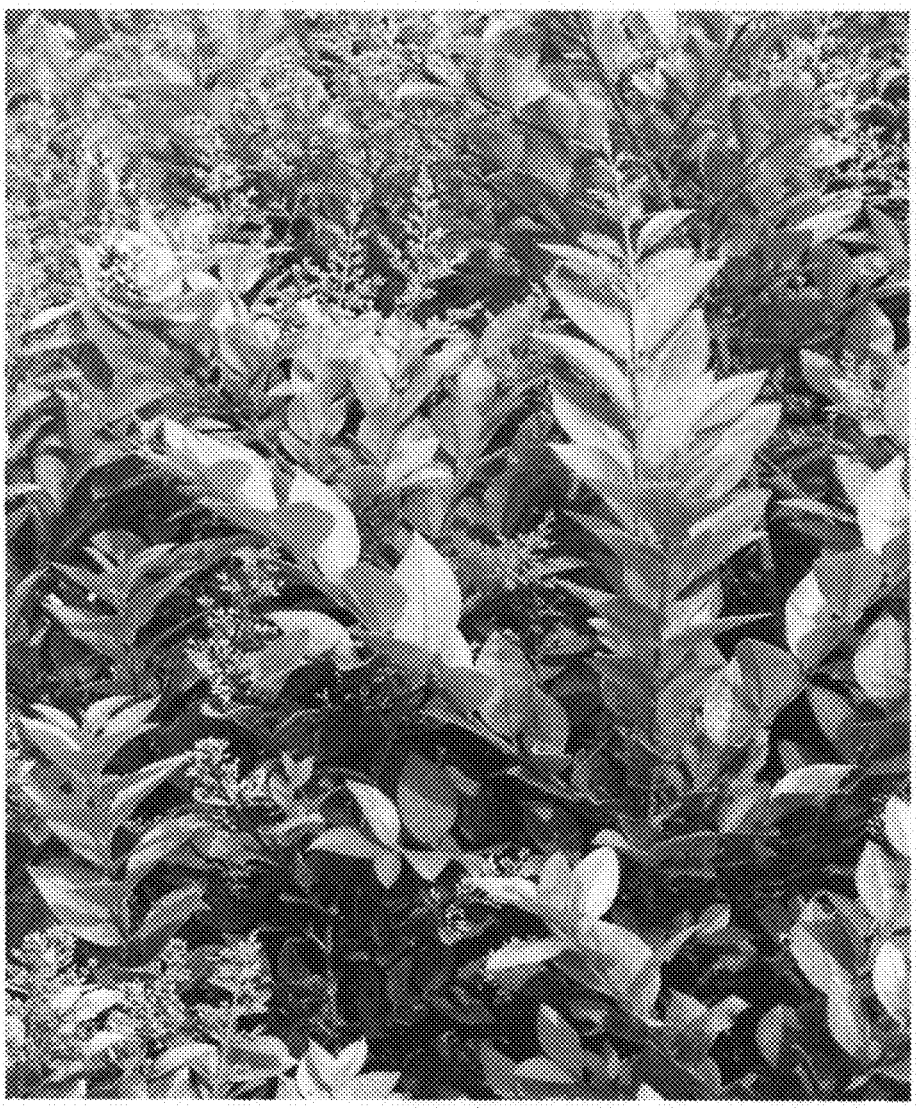
FIG. 2 shows the yellow foliage color of a four-year old plant of 'NCLX1'.
Figure 3:
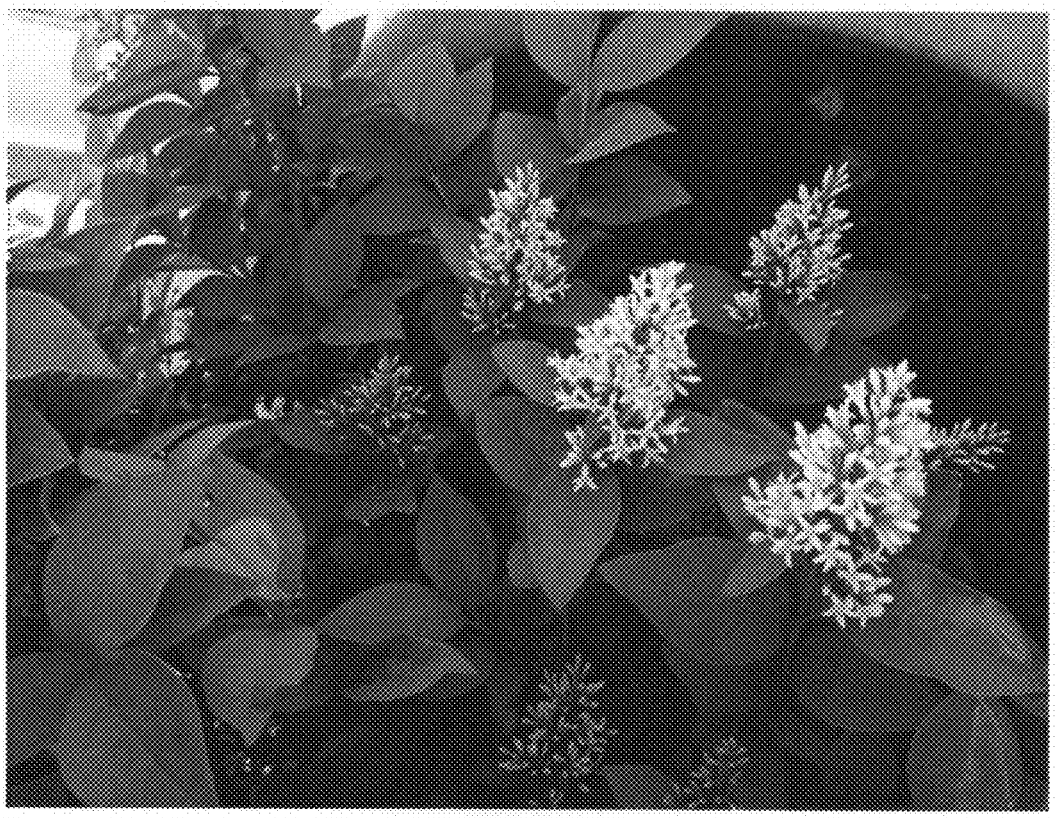
FIG. 3 shows the white flowers of 'NCLX1' and the compactness of the inflorescence on a two-year old plant.

The following detailed description sets forth the distinctive characteristics of 'NCLX1'. The detailed description was taken on 6-year-old plants growing in Mills River, N.C. in May 2014. All colors cited herein refer to The Royal Horticultural Society Colour Chart (The Royal Horticultural Society (R.H.S.), London, 2001 Edition). Where specific dimensions, sizes, colors, and other characteristics are given, it is to be understood that such characteristics are approximations or averages set forth as accurately as practicable.

Classification:

*Botanical name.*—*Ligustrum* 'NCLX1'.

*Common name.*—Privet.

Parentage: *Ligustrum xvicaryi*×*Ligustrum tschonoskii* 'Little Thomas'.

Plant description:

*Growth habit*.—Upright to rounded with compact, dense branching habit.

*Height*.—1.22-1.83 m at maturity.

*Width*.—1.22-1.83 m at maturity.

Stem:

*Immature stem texture*.—Glabrous.

*Immature stem color*.—Yellow-green (144A) flushed with purple (N77C).

*Mature stem texture*.—Glabrous, lenticelled.

*Mature stem color*.—Greyed-green (197A).

*Lateral branch length*.—Average 60 cm, range 30 to 100 cm.

*Lateral branch number*.—50-70 per plant on a three-year old plant.

*Lateral branch strength*.—Strong.

*Lateral branch texture*.—Glabrous with sparse lenticels.

*Lateral branch color*.—RHS Grey-green, 197A.

*Internode length*.—Average 2 cm, range 1 to 5 cm.

Leaves:

*Persistence*.—Deciduous.

*Arrangement*.—Opposite, simple.

*Length*.—Average 3.2 cm, range 1.8 to 4.2 cm.

*Width*.—Average 1.8 cm, range 1 to 2.4 cm.

*Shape*.—Elliptical to ovate.

*Apex*.—Acute.

*Base*.—Rounded.

*Venation pattern*.—Pinnate.

*Margin*.—Entire.

*Emerging leaves*.—Color: Upper and lower: Yellow-green (144A to N144A). Texture: Upper and lower leaves are glabrous.

*Mature leaves during growing season*.—Color: Upper: Yellow-green (N144A). Lower: Yellow-green (145A). Venation: Upper: Yellow-green (N144A). Lower: Yellow-green (N145). Texture: Upper and lower leaves are glabrous.

*Petiole*.—Length: Average 2.5 mm, range 1.0 to 3.5 mm. Width: Average 0.7 mm, range 0.6 to 0.9 mm. Texture: Glabrous. Color: Yellow-green (N144A).

Inflorescence:

*Description*.—Terminal panicle of racemes with multiple flowers.

*Number of flowers per inflorescence*.—30-50.

*Flowering season*.—Late May to June in Mills River, N.C.

*Flower longevity*.—10-14 days.

*Fragrance*.—Light, Sweet.

*Inflorescence height*.—Average 4 cm, range 2-6 cm.

*Inflorescence diameter*.—Average 2.5 cm, range 2-3 cm.

*Flower diameter*.—Average 5.0 mm, range 4.0-6.0 mm.

*Flower depth*.—Average 6.0 mm, range 5.0-7.0 mm.

*Flower buds*.—Length: Less than 8.0 mm. Diameter: Less than 3.0 mm. Shape: Oblong. Color: White (155B).

*Petals*.—Quantity: Four per flower. Length: About 3.0 mm. Width: About 2.0 mm. Shape: Oblong, recurved. Apex: Acute. Base: Fused. Texture: Glabrous. Margin: Entire. Color: White (155B).

*Sepals*.—Quantity: Four per flower. Length: About 3.0 mm. Width: About 1.5 mm. Apex: Acute. Base: Fused. Texture: Glabrous. Color: Yellow-green (145A). Margin: Entire.

*Peduncle*.—Length: About 5.0 mm. Width: About 2.0 mm. Texture: Glabrous. Color: Green (143C).

*Pedicels*.—Length: About 1.5 mm. Width: About 1.0 mm. Texture: Glabrous. Color: Green (143C).

Fruit:

*Description*.—Berry-like drupe.

*Frequency*.—Infrequent, very limited fruit set compared to parental taxa.

*Length*.—About 7.0 mm. Width: About 5.0 mm. Shape: Oblong. Texture: Glabrous.

*Color*.—Black (202A).

Seed: Rarely formed; this description is based on the few seeds that have been observed to date.

*Length*.—0.7 cm.

*Width*.—0.4 cm.

*Shape*.—Oval.

*Color*.—Balk (RHS 203B).

Roots: Dense with fine to medium texture.

Disease and insect resistance: No significant disease or insect pests have been observed to date.

Cold hardiness: At least USDA zone 6b; testing has not been completed in colder zones.

COMPARISON WITH PARENTAL SPECIES

Table 1 shows key distinguishing characteristics between 'NCLX1' and its parental taxa. 'NCLX1' is distinguished from *Ligustrum xvicaryi* in that 'NCLX1' has more compact inflorescences, a more compact habit, and has very limited fruit production. 'NCLX1' is distinguished from *Ligustrum tschonoskii* 'Little Thomas' by having bright yellow mature leaf color and later flowering time.

TABLE 1

Comparison to parental taxa.

| | Taxa | | |
|---|---|---|---|
| Trait | *Ligustrum* × *vicaryi* | *Ligustrum tschnoskii* 'Little Thomas' | *Ligustrum* 'NCLX1' |
| Growth habit | Vase-shaped, somewhat rangy shrub | Rounded, spreading shrub | Upright, compact shrub |
| Mature size | 10-12' tall × 8-10' wide | 4-6' tall × 6-8' wide | 4-6' tall × 4-6' wide |
| Emerging foliage color | Upper: Yellow-green (N144A) Lower: Yellow-green (146D) | Upper and Lower: Yellow-green (144A) | Upper and Lower: Yellow-green (144A to N144A) |
| Mature foliage color | Upper and lower: Yellow-green (151A) | Upper: Green (138A) Lower: Yellow-green (146B) | Upper: Yellow-green (N144A) Lower: Yellow-green (145A) |
| Flowering season | Early to mid-June | Mid- to late May | Early to mid-June |
| Number of flowers per inflorescense | About 100, ranges from 50 to 180 | About 45, ranges from 25 to 90 | About 35, ranges from 10 to 80 |
| Inflorescence height | About 6 cm, ranges from 4 to 7 cm | About 4 cm, ranges from 2 to 6 cm | About 4 cm, ranges from 2 to 6 cm |
| Fragrance | Light, sweet fragrance | Light, acrid fragrance | Light, sweet fragrance |
| Seed production | Prolific | Prolific | Infrequent |

What is claimed is:

1. A new and distinct privet plant named 'NCLX1' substantially as illustrated and described herein.

* * * * *